United States Patent
Ardenkjaer-Larsen et al.

(10) Patent No.: US 8,003,077 B2
(45) Date of Patent: Aug. 23, 2011

(54) METHOD FOR THE PRODUCTION OF HYPERPOLARIZED $^{129}$XE

(75) Inventors: Jan-Henrik Ardenkjaer-Larsen, Malmo (SE); Lennart Hansson, Malmo (SE); Haukur Johannesson, Malmo (SE); Rolf Servin, Malmo (SE); Lars-Goran Wistrand, Malmo (SE)

(73) Assignee: GE Healthcare AS, Oslo (NO)

( * ) Notice: Subject to any disclaimer, the term of this patent is extended or adjusted under 35 U.S.C. 154(b) by 1580 days.

(21) Appl. No.: 10/532,563

(22) PCT Filed: Oct. 24, 2003

(86) PCT No.: PCT/NO03/00352
§ 371 (c)(1),
(2), (4) Date: Dec. 5, 2005

(87) PCT Pub. No.: WO2004/037296
PCT Pub. Date: May 6, 2004

(65) Prior Publication Data
US 2006/0173282 A1    Aug. 3, 2006

(30) Foreign Application Priority Data
Oct. 25, 2002    (NO) .................................. 20025124

(51) Int. Cl.
*A61B 5/055*    (2006.01)
*A61B 5/05*    (2006.01)

(52) U.S. Cl. ......................................... 424/9.3; 600/410
(58) Field of Classification Search .................. 424/9.3; 600/410
See application file for complete search history.

(56) References Cited

U.S. PATENT DOCUMENTS

| 6,426,058 | B1 * | 7/2002 | Pines et al. ..................... 424/9.3 |
| 6,466,814 | B1 * | 10/2002 | Ardenkjaer-Larsen et al. ............................ 600/420 |

FOREIGN PATENT DOCUMENTS

| WO | 98/58272 | 12/1998 |
| WO | 99/35508 | 7/1999 |
| WO | 00/23797 | 4/2000 |
| WO | 01/55656 | 8/2001 |

OTHER PUBLICATIONS

Herald E. Moller, et.al., "MRI of the lungs Using Hyperpolarized Noble Gases" Magnetic Resonance in Medicine, vol. 47, 2002 pp. 1029-1051.
A. Honig, "High Equilibrium Spin Polarizations in Solid 129Xe" Physica B, (2000) 2049-2050.
International Search Report for PCT/NO2003/00352 dated Mar. 22, 2004.

* cited by examiner

*Primary Examiner* — Michael G Hartley
*Assistant Examiner* — Leah Schlientz
(74) *Attorney, Agent, or Firm* — Robert F. Chisholm

(57) ABSTRACT

The present invention relates to a method for the production of hyperpolarized $^{129}$Xe and to a method for the production of a contrast agent.

8 Claims, No Drawings

METHOD FOR THE PRODUCTION OF HYPERPOLARIZED $^{129}$XE

This application is a filing under 35 U.S.C. 371 of international application number PCT/NO2003/000352, filed Oct. 24, 2003, which claims priority to application number 20025124 filed Oct. 25, 2002, in Norway the entire disclosure of which is hereby incorporated by reference.

The present invention relates to a method for the production of hyperpolarized $^{129}$Xe and to a method for the production of a contrast agent.

$^{129}$Xe is a gas at room temperature. The nucleus has a spin quantum number of ½, and a moderately large nuclear magnetic moment of −1.347494 nuclear magnetons. It can be taken up into the lungs and absorbed into blood or tissue. It has been recognized that it has potential to be imaged in the body via magnetic resonance imaging (MRI). However, since the gas phase is approximately 1000 times less dense (in moles/liter) than the condensed phase of biological material (e.g. blood, tissue), its nuclear magnetic resonance (NMR) signal is much weaker than that of the protons in the condensed biological material. To surmount this, hyperpolarized $^{129}$Xe has been prepared. In this case, the nuclear magnetization, upon which the MRI sensitivity depends, can be increased by 5 orders of magnitude, making the contrast available with the $^{129}$Xe even in the gas phase larger than that from the protons in their equilibrium room temperature condensed phases. Because the spin is ½, the retention time of the non-equilibrium highly polarized state of the hyperpolarized $^{129}$Xe, frequently referred to as the spin-lattice relaxation time $T_1$, is long enough even at body temperature for the $^{129}$Xe to persist in the hyperpolarized state for sufficient time to obtain contrast enhanced MR images. Thus, hyperpolarized $^{129}$Xe gas has generated considerable interest as an inhalable contrast agent for magnetic resonance imaging of the lungs.

W. Happer et al., Phys. Rev. A29, 3092 (1984) described the production of hyperpolarized $^{129}$Xe using optical pumping laser techniques. A disadvantage of this method is the low production rate, due to polarization being achieved in the low density gaseous phase. Thus, only rates of a few liters per hour are achievable.

WO-A-99/35508 discloses hyperpolarization of xenon in the solid state using the "brute force" method or the dynamic nuclear polarization (DNP) method.

WO-A-00/23797 discloses additional methods for the hyperpolarization of xenon in the solid state, such as doping xenon with paramagnetic oxygen molecules, irradiating the xenon with ionizing radiation or the dispersal of magnetized small particles encapsulated in polymers which are placed in the xenon.

It has now surprisingly been found that the presence of an additive in DNP hyperpolarization of xenon in the solid state dramatically increases polarization enhancement.

The present invention provides a method for producing hyperpolarized $^{129}$Xe comprising
a) preparing a mixture of xenon, an additive and a free radical
b) hyperpolarizing said mixture according to the DNP method to obtain hyperpolarized $^{129}$Xe and
c) optionally separating said xenon from the other components of the mixture.

In a first step a) a mixture of xenon, an additive and a free radical is prepared.

According to the invention, xenon can be used in its natural form, i.e. a mixture of several isotopes including $^{131}$Xe (21.2%) and $^{129}$Xe (26.4%). Alternatively, $^{129}$Xe enriched xenon can be used.

The term "additive" according to the invention encompasses also suitable mixtures of additives. Preferably, at least one solvent or a mixture of solvents is used as an additive in the method according to the invention. More preferably, at least one solvent or a mixture of solvents is used which has good glass-forming properties, e.g. single chained alcohols like ethanol or propanol or glycols and/or lipophilic properties, e.g. like toluene or methylcyclohexane. Further preferred are solvents or mixtures of solvents which contain a high amount of NMR active nuclei such as $^1$H, $^{19}$F, $^{31}$P and the like. Particularly preferably, the additive is at least one solvent selected from the group consisting of straight chain or branched $C_6$-$C_{12}$-alkanes, $C_5$-$C_{12}$-cycloalkanes, fatty alcohols, fatty esters, substituted benzene derivatives like toluene or xylene, mono- or polyfluorinated solvents like tetradecafluorohexane or hexafluoroisopropanol, single chained alcohols like ethanol, propanol or butanol and glycols. Most preferred additives are cyclopentane, toluene, xylene, ethanol, propanol and 2-butanol.

In a preferred embodiment, the additive is chosen as such that there is a temperature/pressure region where both the additive and Xenon are simultaneously in the liquid state. Both propanol and ethanol are suitable examples of such additives.

In a further preferred embodiment, the amount of xenon in the mixture of xenon and additive is kept low, as the obtained $^{129}$Xe polarization decreases when the concentration of xenon in the mixture of xenon and additive is increased. However, since the intensity of the NMR signal is determined by both polarization (which increases with dilution) and the number of $^{129}$Xe spins (with decreases with dilution), these two factors have to be balanced when choosing the amount of xenon for the DNP polarization.

The free radical in the mixture of step a) may either be a stable free radical such as a nitroxide or a trityl radical or a free radical prepared in situ from a stable radical precursor by a radical-generating step shortly before the hyperpolarization step b), or alternatively by the use of ionising radiation. Suitable free radicals are organic free radicals such as triarylmethyl, nitroxide radicals such as porphyrexide, TEMPO, TEMPONE and TEMPOL (see below), oxygen centered radicals such as galvinoxyl (see below), carbon centered radicals such as trityls and allyls, metal ions with unpaired electrons such as Cr(V), e.g. BHHA-Cr(V) and EHBA-Cr(V) (see below), Mn(II), e.g. MnCl$_2$, Tm(II), Yb(III), Nd(III), V(IV), Ni(II) and Fe(III) ions or radiation generated radical centers and biradicals, e.g. those described in WO-A-88/10419, WO-A-90/00904, WO-A-91/12024, WO-A-93/02711 and WO-A-96/39367. Preferred free radicals are those which dissolve in the additive and/or in liquid Xenon. Particularly preferred free radicals are trityls and nitroxide radicals, e.g. tert.-amyl-tert.-butyl nitroxide.

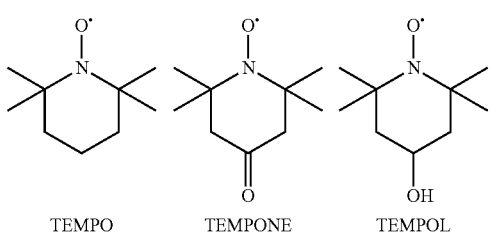

TEMPO     TEMPONE     TEMPOL

-continued

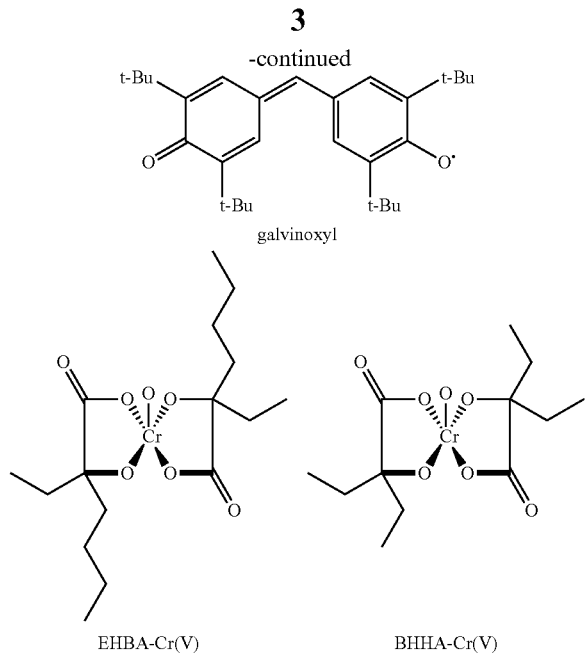

EHBA-Cr(V)   BHHA-Cr(V)

In a preferred embodiment, xenon gas is condensed on top of the additive and free radical in a suitable reaction vessel, preferably by using a liquid nitrogen bath. The reaction vessel is subsequently sealed and warmed up until the components are in the liquid state. The additive and the free radical are mixed with the liquid xenon until a homogeneous mixture is obtained. The formation of a homogeneous mixture may be achieved by several means known in the art such as agitation, shaking, stirring and the like. The resulting mixture is then cooled rapidly, e.g. in a liquid nitrogen bath, and the solid obtained is used for the hyperpolarization.

In a second step b), the mixture of step a) is hyperpolarized according to the DNP method to obtain hyperpolarized $^{129}$Xe.

Suitably, the mixture will be cooled, e.g. in liquid nitrogen, in order to result a solid which can be used for the DNP hyperpolarization.

DNP mechanisms include the Overhauser effect, the so-called solid effect and the thermal mixing effect. During the DNP process, energy, normally in the form of microwave radiation, is provided. There is a transfer of polarization from the unpaired electron of the radical to $^{129}$Xe and/or the NMR active nuclei of the additive, depending on the properties of the free radical and/or the frequency of the microwave radiation applied. If the NMR active nuclei of the additive are polarized, this polarization may be transferred to $^{129}$Xe subsequently by a suitable cross-polarization sequence. The DNP method may utilize a moderate or high magnetic field and a very low temperature, e.g. by carrying out the DNP process in liquid helium and a magnetic field of about 1 T or above. The temperature should be very low, e.g. 100 K or less, preferably 4.2 K or less, more preferably 1.5 K or less, especially preferably 1 K or less and even more especially preferably 100 mK or less. The magnetic field strength used should be as high as possible, suitably higher than 0.1 T, preferably higher than 1 T, more preferably 5 T or more, especially preferably 15 T and more and most preferably 20 T and more. Alternatively, a moderate magnetic field and any temperature at which sufficient enhancement is achieved may be employed. Preferably, the polarization should 1% or more, more preferably 10% and more, especially preferably 25% and more and most preferably 50% and more.

After hyperpolarization xenon may be separated from the other components of the mixture by simply warming the mixture until xenon is in a gaseous state and collecting the gas in a suitable container. Warming of the mixture can be achieved by different means such as contacting the mixture with a hot liquid like water, or using laser or microwave energy to melt the mixture. Such means for dissolving and melting hyperpolarised solid samples are described in WO-A-02/37132 and WO-A-02/36006. Optionally, the obtained xenon gas can be condensed again to obtain "xenon ice" which can be transported using a permanent magnet and a liquid nitrogen bath. Preferably, the magnetic field strength for such a transport should be as high as possible, suitably 10 mT or more, preferably 0.1 T or more, more preferably 0.2 T or more and especially preferably 0.3 T or more. The temperature for such a transport should be below the boiling point of xenon, i.e. below 166.05 K at atmospheric pressure.

For the use as a contrast agent, the condensed xenon may conveniently be heated prior to its use.

Thus, another aspect of the invention is a method for the production of a contrast agent comprising
a) preparing a mixture of xenon, an additive and a free radical
b) hyperpolarizing said mixture according to the DNP method to obtain hyperpolarized $^{129}$Xe
c) separating xenon from the other components of the mixture, and
d) optionally condensing the separated xenon again.

Yet another aspect of the invention is the use of DNP-hyperpolarized $^{129}$Xe for the manufacture of a contrast agent for the use in magnetic resonance imaging of the human or non-human animal body, preferably of the lungs of the human or non-human animal body.

Yet another aspect of the invention is a method for magnetic resonance imaging of the lungs of a human or non-human animal body comprising
a) preparing a mixture of xenon, an additive and a free radical
b) hyperpolarizing said mixture according to the DNP method to obtain hyperpolarized $^{129}$Xe
c) separating said xenon from the other components of the mixture,
d) optionally condensing and heating said separated xenon
e) administering said xenon to the lungs of a human or non-human animal body and
f) generating magnetic resonance images of said body.

Yet another aspect of the invention is the use of $^{129}$Xe which has been hyperpolarized according to the method of the invention as a contrast agent, more preferably as a contrast agent for magnetic resonance imaging of the lungs.

EXAMPLES

Example 1

Comparison Example

10 μl of tert.-amyl-tert.-butyl-nitroxide in a reaction vessel were cooled in a liquid nitrogen bath. 750 ml of gaseous xenon (natural abundance $^{129}$Xe, STp (=standard temperature and pressure)) were condensed into the reaction vessel. The reaction vessel was sealed and the temperature was adjusted to 195 K. The content was agitated until a homogeneous liquid was formed and then cooled down in a liquid nitrogen bath. The reaction vessel and the liquid nitrogen bath were then moved to a N$_2$-glove box. The reaction vessel was opened and liquid nitrogen was added. The solid content of the reaction vessel was pulverized with a spatula and transferred to a pre-cooled sample holder. The sample was then rapidly inserted into a cryostat and DNP polarization was performed using a magnetic field of 3.35 T, an irradiation frequency of 93.3 GHz and a temperature of 1.6 K.

$T_1$ was measured to ca. 10 h at 1.6 K and 3.35 T. No DNP effect was observed.

Example 2

Comparison Example

Example 2 was carried out as Example 1 using 100 μl of tert.-amyl-tert.-butyl-nitroxide. $T_1$ was measured to ca. 1 h at 1.6 K and 3.35 T. No DNP effect was observed.

Example 3

Example 3 was carried out as Example 1 using 10 μl of tert.-amyl-tert.-butyl-nitroxide in 1.2 ml toluene and 800 ml of gaseous $^{129}$Xe. DNP polarization was performed using a magnetic field of 3.35 T, an irradiation frequency of 93.3 GHz and a temperature of 1.44 K. A polarization enhancement of 24 was measured at 1.44 K and 3.35 T, corresponding to a polarization of $^{129}$Xe of 1.6%.

Example 4

Sample:
1.5 ml propanol, 26 mg Tris-(8-ethoxycarbonyl-2,2,6,6-tetralis-(methylbenzo[1,2-d:4,5-d']bis(1,3)dithiole)methyl, in the following named "radical", 500 ml (STP) natural abundance xenon.

Description of Experiment:
The Radical and propanol were inserted into a round bottom flask that was subsequently the flask evacuated from air and flushed with helium gas several times to reduce the contents of oxygen in the system. The flask was then immersed in a liquid nitrogen bath and xenon gas was allowed to condense into the flask. After sealing the flask, the liquid nitrogen bath was replaced by an ethanol/$CO_2$ bath. The content of the flask was agitated by magnetic stirring. The ethanol/$CO_2$ bath was then replaced by an ethanol bath and cooled to 163 K using liquid nitrogen. At this temperature both propanol and xenon are in the liquid phase and the content of the flask was a viscous liquid. Additional magnetic stirring was performed followed by rapid cooling in a liquid nitrogen bath. The flask was opened and liquid nitrogen was added. The obtained solid content of the flask was pulverized with a pre-cooled spatula and transferred to a pre-cooled sample holder. The sample was rapidly inserted into a cryostat and DNP polarization was performed using a magnetic field of 3.354 T, an irradiation frequency of 93.93 GHz (200 mW) and a temperature of 1.08 K.

Results:
The obtained DNP enhancement was a factor of 82 compared to the thermal equilibrium signal, which corresponds to a polarization equal to 7.2%. The time constant for polarization build-up was 1.2 hours, and the $T_1$ was estimated to be 4.2 hours.

Example 5

Sample:
3.85 ml propanol, 52 mg Radical, 500 ml (STP) natural abundance xenon (corresponding to 0.85 ml liquid xenon).

Description of Experiment:
The experiment was performed in the same way as Example 4.

Results:
The obtained DNP enhancement was a factor of 263.4 compared to the thermal equilibrium signal, which corresponds to a polarization equal to 23.2%. The time constant for polarization build-up was 2.2 hours, and the $T_1$ was estimated to be 4.6 hours.

Example 6

Sample:
1.0 ml propanol, 20.5 mg Radical, 500 ml (STP) natural abundance xenon.

Description of Experiment:
The experiment was performed in the same way as Example 4.

Results:
The obtained DNP enhancement was a factor of 26 compared to the thermal equilibrium signal, which corresponds to a polarization equal to 2.3%. The time constant for polarization build-up was 1.2 hours, and the $T_1$ was estimated to be 2.5 hours.

Example 7

Sample:
3.85 ml propanol, 52.7 mg Radical, 500 ml (STP) $^{129}$Xe-enriched xenon (82.3% $^{129}$Xe).

Description of Experiment:
The experiment was performed in the same way as Example 4.

Results:
The obtained DNP enhancement was a factor of 197 compared to the thermal equilibrium signal, which corresponds to a polarization equal to 17.4%. The time constant for polarization build-up was 1.7 hours, and the $T_1$ was estimated to be 6.2 hours.

Example 8

Sample:
3.85 ml ethanol (99.5%), 52.2 mg Radical, 500 ml (STP) natural abundance xenon.

Description of Experiment:
The experiment was performed in the same way as Example 4.

Results:
The obtained DNP enhancement was a factor of 171.6 compared to the thermal equilibrium signal, which corresponds to a polarization equal to 15.2%. The time constant for polarization build-up was 4.1 hours, and the $T_1$ was estimated to be 4.4 hours.

Example 9

Sample:
3.85 ml 2-butanol, 51.4 mg Radical, 500 ml (STP) natural abundance xenon.

Description of Experiment:
The experiment was performed in the same way as Example 4.

Results:
The obtained DNP enhancement was a factor of 23 compared to the thermal equilibrium signal, which corresponds to a polarization equal to 2.0%. The time constant for polarization build-up was 1.5 hours, and the $T_1$ was estimated to be 3.9 hours.

Example 10

Sample: Same preparation as in Example 5.
Description of Experiment:
The initial part of the experiment was performed as in Example 5, except that the irradiation frequency was 93.945 GHz. The sample was polarized for 2 hours and subsequently thawed in situ using hot water (≈95° C.). The xenon gas was collected in a bag normally used for storage of hyperpolarized helium gas. The xenon gas was then transferred into a 10 mm NMR tube which had been pre-filled with argon. The NMR tube was sealed with a cap, and transferred to a 9.4 Tesla NMR spectrometer for detection.
Results:
The DNP enhancement in the solid state was not determined. The time constant for polarization build-up was approximately one hour. The obtained polarization enhancement in the gas phase was a factor of 4752 compared to the thermal equilibrium signal at room temperature, which corresponds to a polarization equal to 4.3%.

What is claimed is:

1. A method for producing hyperpolarized $^{129}$Xe comprising
   a) preparing a mixture of xenon, at least one solvent or a mixture of solvents selected from the group of single chain alcohols glycols, toluene, cyclopentane and methylcyclohexane, and a free radical
   b) hyperpolarizing said mixture according to the DNP method to obtain hyperpolarized $^{129}$Xe and
   c) optionally separating said xenon from the other components of the mixture.

2. A method according to claim 1, wherein the mixture in step a) is prepared from liquid xenon.

3. A method according to claim 1, wherein the mixture in step a) is prepared by condensing xenon gas on the top of the at least one solvent or mixture of solvents and the free radical, warming the components until xenon and the at least one solvent or mixture of solvents are in a liquid state and mixing the components until a homogeneous mixture is obtained.

4. A method according to claim 1, wherein in step b) $^{129}$Xe is directly hyperpolarized.

5. A method according to claim 1, wherein in step b) the NMR active nuclei of the at least one solvent or mixture of solvents are hyperpolarized and this polarization is subsequently transferred to $^{129}$Xe by a cross-polarization sequence.

6. A method according to claim 1, wherein xenon enriched with $^{129}$Xe is used.

7. A method according to claim 1, wherein in step c) xenon is separated from the other components of the mixture by warming the mixture until xenon is in the gas state and collecting said xenon in a suitable container.

8. A method for the production of a contrast agent comprising
   a) preparing a mixture of xenon, at least one solvent or a mixture of solvents selected from the group of single chain alcohols, glycols, toluene, cyclopentane and methylcyclohexane, and a free radical;
   b) hyperpolarizing said mixture according to the DNP method to obtain hyperpolarized $^{129}$Xe
   c) separating said xenon from the other components of the mixture, and
   d) optionally condensing the separated xenon again.

* * * * *